US009066677B2

(12) United States Patent
Seto

(10) Patent No.: US 9,066,677 B2
(45) Date of Patent: Jun. 30, 2015

(54) ILLUMINATION UNIT AND ENDOSCOPIC APPARATUS

(75) Inventor: Yasuhiro Seto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 27 days.

(21) Appl. No.: 13/296,913

(22) Filed: Nov. 15, 2011

(65) Prior Publication Data

US 2012/0123213 A1    May 17, 2012

(30) Foreign Application Priority Data

Nov. 16, 2010   (JP) ................. 2010-256324

(51) Int. Cl.
*A61B 1/06* (2006.01)
*H01L 27/146* (2006.01)
*A61B 1/04* (2006.01)

(52) U.S. Cl.
CPC ............. *A61B 1/0638* (2013.01); *A61B 1/0653* (2013.01); *A61B 1/063* (2013.01)

(58) Field of Classification Search
CPC ................. H05B 33/0845; H05B 33/0869
USPC ................ 600/178, 180, 181; 250/370.08; 315/291, 308; 362/230, 231, 572, 574
See application file for complete search history.

(56) References Cited

U.S. PATENT DOCUMENTS

| | | | |
|---|---|---|---|
| 2005/0099824 | A1 | 5/2005 | Dowling et al. |
| 2009/0062617 | A1 | 3/2009 | Mizuyoshi |
| 2010/0240953 | A1 | 9/2010 | Murakami |
| 2011/0034770 | A1* | 2/2011 | Endo et al. ............ 600/118 |

FOREIGN PATENT DOCUMENTS

| | | |
|---|---|---|
| EP | 2 030 559 A1 | 3/2009 |
| JP | 2002-112962 A | 4/2002 |

(Continued)

OTHER PUBLICATIONS

Japanese Office Action issued in JP 2010-256324, dated Sep. 13, 2013 with a partial English translation.

(Continued)

*Primary Examiner* — Anhtuan T Nguyen
*Assistant Examiner* — Aaron B Fairchild
(74) *Attorney, Agent, or Firm* — Birch, Stewart, Kolasch & Birch, LLP

(57) ABSTRACT

An illumination unit includes semiconductor light sources, a target light quantity setting unit for setting a target light quantity for a total outgoing light quantity, a light quantity ratio setting unit for setting an outgoing light quantity ratio among the semiconductor light sources, an amplitude value setting unit for setting amplitude values of driving signals for the semiconductor light sources based on the set outgoing light quantity ratio and a driving signal generating unit for generating the driving signals by use of common pulse modulation control while keeping the set amplitude values. When the target light quantity is set, a driving pulse signal corresponding to the target light quantity is set in common among the semiconductor light sources. The driving pulse signal is formed to have amplitude values corresponding to the outgoing light quantity ratio to generate individual driving signals for driving the semiconductor light sources respectively.

10 Claims, 8 Drawing Sheets

(56) References Cited

FOREIGN PATENT DOCUMENTS

| | | |
|---|---|---|
| JP | 2005-347223 A | 12/2005 |
| JP | 2006-218283 A | 8/2006 |
| JP | 2007-139822 | 6/2007 |
| JP | 2009-56248 A | 3/2009 |
| JP | 2010-046354 A | 3/2010 |
| JP | 2010-213993 A | 9/2010 |

OTHER PUBLICATIONS

Japanese Office Action issued in corresponding JP Application No. 2013-250696, dated Sep. 2, 2014, with a partial English translation.

Chinese Office Action issued in corresponding CN 201110363146.9 on Aug. 5, 2014, with an English translation.

Chinese Second Office Action issued in corresponding CN 201110363146.9 on Mar. 9, 2015, with an English translation.

* cited by examiner

ILLUMINATION UNIT AND ENDOSCOPIC APPARATUS

CROSS-REFERENCE TO RELATED APPLICATIONS

This application claims the benefit of Japanese Patent Application No. 2010-256324, filed on Nov. 16, 2010, the entire contents of which are hereby incorporated by reference, the same as if set forth at length; the entire of which are incorporated herein by reference.

BACKGROUND OF THE INVENTION

1. Technical Field

The present invention relates to an illumination unit and an endoscopic apparatus provided with the same.

2. Description of Related Art

Endoscopic apparatus for observing tissues in a body cavity has been known broadly. Generally, an endoscopic apparatus has a configuration in which white light emitted from a white light source such as a xenon lamp is supplied as illumination light to a to-be-observed region in a body cavity through a light guide and an image based on reflected light from the to-be-observed region irradiated with the white light is captured by an imaging device to generate an observation image. In recent years, an endoscopic apparatus having observation modes using special light is also being used. The observation modes are narrow-band light observation for observing blood capillaries or microscopic structures in a tissue surface layer while biological tissues are irradiated with narrow-band light with a specific wavelength, fluorescent observation using intrinsic fluorescence or drug fluorescence, etc. As a light source of an endoscopic apparatus for irradiation with special light, there has been known a configuration in which light emitted from a white light source such as a xenon lamp is made to pass through a rotary filter having a predetermined light absorption property to selectively extract light in a desired wavelength band so that a subject is irradiated with the extracted light (see JP-A-2006-218283). In the endoscopic apparatus having the aforementioned configuration, B light with a narrow-band wavelength and G light with a narrow-band wavelength, as special light for narrow-band light observation, can be emitted at a predetermined outgoing light quantity ratio. The intensity of the special light in this case is adjusted by an aperture unit provided on the way of an optical path from the white light source. The outgoing light ratio between the B light and the G light is set by light transmittances of a B filter and a G filter in the rotary filter.

SUMMARY

However, the intensity of light outputted from a light source is generally lowered due to deterioration with age. Thus, the outgoing light quantity ratio between the B light and the G light defined by the transmittances of the rotary filter may change to break wavelength balance in outgoing light. The wavelength balance in the outgoing light affects the degree of reflection of a feature quantity component in an observation image. When the outgoing light is out of desired wavelength balance, there may be a case in which a feature quantity cannot be observed satisfactorily.

Therefore, semiconductor light sources including semiconductor light emitting devices such as laser light sources or light emitting diodes which have long lives and small output fluctuations may be used in place of the white light source such as a xenon lamp. In this case, outputs of the semiconductor light sources can be controlled so finely that the wavelength balance can be set with high accuracy. However, in intensity modulation, it is difficult to perform the intensity modulation on a plurality of semiconductor light sources while keeping the wavelength balance among the semiconductor light sources with high accuracy. For example, light quantity control can be performed with high accuracy using a narrow pulse generator or a high-resolution type PWM controller. However, either device is too expensive to be mounted on an endoscopic apparatus practically in view of cost.

Thus, in fact, there still remain many problems as to how to control light quantities of semiconductor light sources at least equivalently to that of a white light source such as a xenon lamp.

An object of the invention is to provide an illumination unit in which a plurality of semiconductor light sources can be controlled with high accuracy in accordance with a target light quantity without breaking balance in outgoing light quantity ratio among the semiconductor light sources, and an endoscopic apparatus having the illumination unit.

The invention has the following configurations.

(1) An illumination unit includes a plurality of semiconductor light sources, a target light quantity setting unit, a light quantity ratio setting unit, an amplitude value setting unit and a driving signal generating unit. The plurality of semiconductor light sources emit lights with different spectra from each other in accordance with inputted driving signals. The target light quantity setting unit sets a target light quantity for a total outgoing light quantity which is obtained by summing up quantities of the lights emitted from the semiconductor light sources. The light quantity ratio setting unit sets an outgoing light quantity ratio among the semiconductor light sources. The amplitude value setting unit sets amplitude values of driving signals for the semiconductor light sources, respectively, based on the set outgoing light quantity ratio. The driving signal generating unit generates the driving signals by use of common pulse modulation control corresponding to the target light quantity while keeping the set amplitude values.

(2) An endoscopic apparatus includes an illumination optical system and an imaging optical system. The illumination optical system outgoes light emitted from the illumination unit according to (1), from a front end of an endoscope insertion portion. The imaging optical system obtains an observation image of a subject.

According to the illumination unit and the endoscopic apparatus having the same according to the invention, it is possible to control a plurality of semiconductor light sources with high accuracy in accordance with a target light quantity without breaking balance in outgoing light quantity ratio among the semiconductor light sources. Thus, illumination light of an endoscope for normal observation or special light observation can be set accurately at any intensity while keeping a desired outgoing light quantity ratio.

DETAILED DESCRIPTION OF EMBODIMENTS OF THE INVENTION

An embodiment of the invention will be described below in detail with reference to the drawings.

Figure 1:
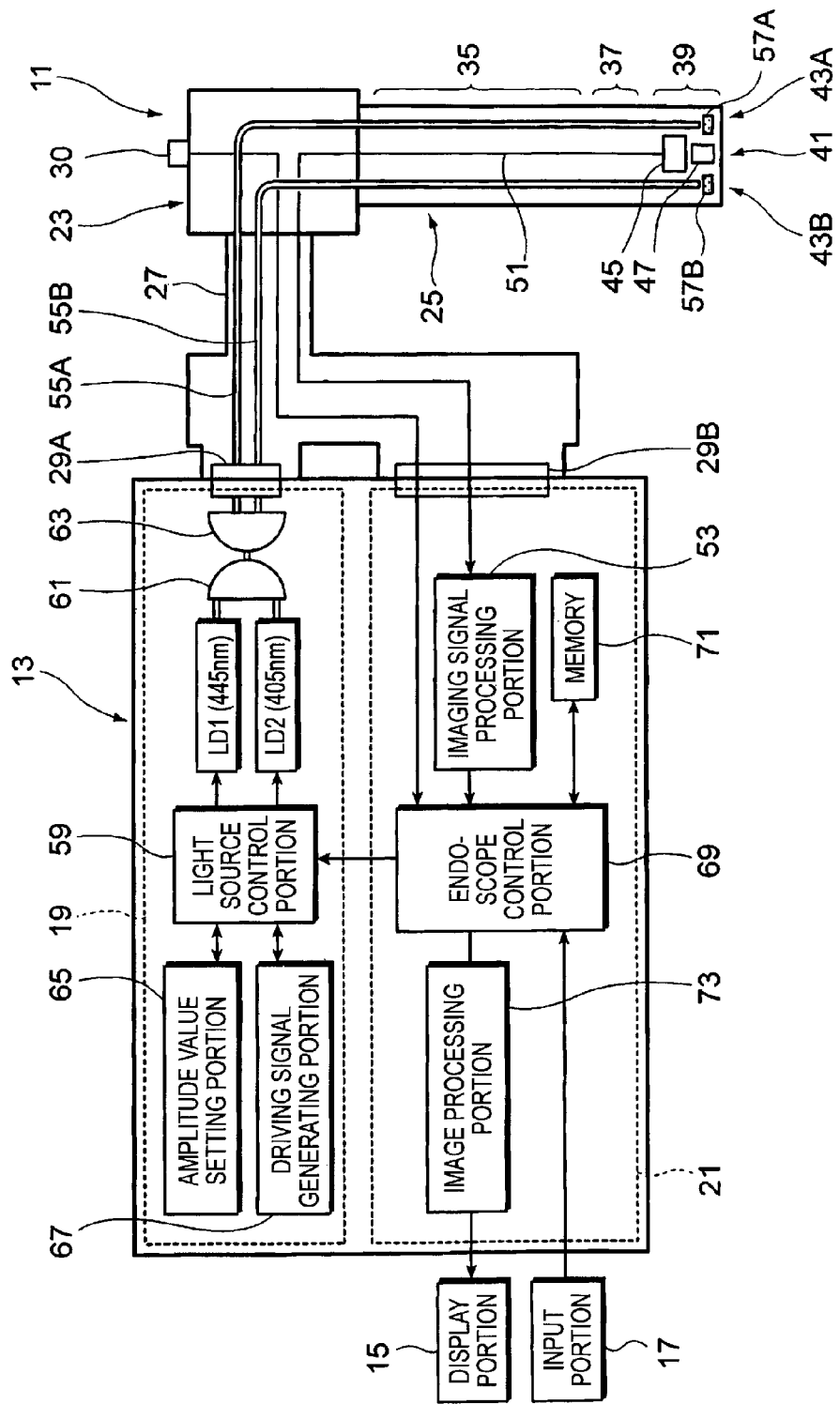
FIG. 1 is a diagram showing a configuration of an endoscopic apparatus including an endoscope and each unit the endoscope is connected to, in order to explain an embodiment of the invention.
Figure 2:
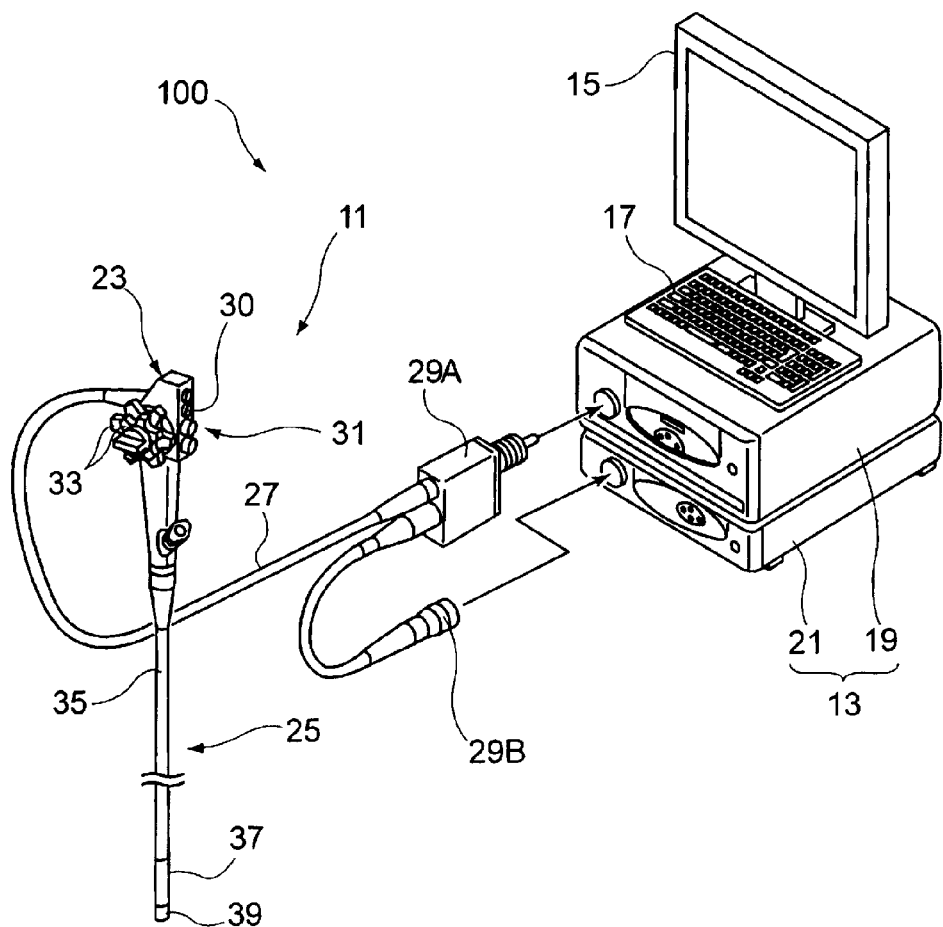
FIG. 2 is an external view showing a specific configuration example of the endoscopic apparatus.

FIG. 1 is a view for explaining an embodiment of the invention, showing a configuration of an endoscopic apparatus having an endoscope and units the endoscope is connected to. FIG. 2 is an external view showing a specific example of the configuration of the endoscopic apparatus.

As shown in FIG. 1, an endoscopic apparatus 100 includes an endoscope 11, a control unit 13, a display portion 15 such as a monitor, and an input portion 17 such as a keyboard or a mouse for inputting information into the control unit 13. The control unit 13 includes a light source unit 19 and a processor 21 for performing signal processing on a captured image.

The endoscope 11 has a body operation portion 23 and an insertion portion 25 which is connected to the body operation portion 23 in order to be inserted into a subject (body cavity). A universal cable 27 is connected to the body operation portion 23. A front end of the universal cable 27 is connected to the light source unit 19 through a light guide (LG) connector 29A. In addition, the front end of the universal cable 27 is connected to the processor 21 through a video connecter 29B.

As shown in FIG. 2, a pair of angle knobs 33 as well as various operation buttons 31 such as buttons for sucking, feeding air and feeding water in the front end side of the insertion portion 25, a shutter button for capturing an image and an observation mode changeover button 30 for switching the observation modes, etc. are provided in the body operation portion 23 of the endoscope 11.

The insertion portion 25 is constituted by a soft portion 35, a bendable portion 37 and a front end portion (endoscope front end portion) 39 in ascending order of distance from the body operation portion 23. When the angle knobs 33 of the body operation portion 23 are turned, the bendable portion 37 is remotely operated to be bent. Thus, the front end portion 39 can be steered in a desired direction.

As shown in FIG. 1, an observation window 41 of an imaging optical system and light irradiation windows 43A, 43B of an illumination optical system are disposed in the endoscope front end portion 39. An observation image captured thus is displayed on the monitor 17 connected to the processor 15. Light reflected from a subject irradiated with illumination light from each light irradiation window 43A, 43B passes through the observation window 41 and is captured as an image by an imaging device 45. An observation image captured thus is displayed on the display portion 15 connected to the processor 21.

Here, the imaging optical system has the imaging device 45 such as a CCD (Charge Coupled Device) type image sensor or a CMOS (Complementary Metal-Oxide Semiconductor) type image sensor and an optical member 47 such as a lens for focusing an observation image on the imaging device 45. The observation image focused on a light reception surface of the imaging device 45 and taken in by the imaging device 45 is converted into an electric signal, which is inputted to an imaging signal processing portion 53 of the processor 21 through a signal cable 51, and converted into a video signal in the imaging signal processing portion 53. Although the details will be described later, the imaging signal processing portion 53 functions as a light quantity detecting unit for detecting the light quantity of an image of a subject based on an imaging signal outputted from the imaging device 45.

On the other hand, the illumination optical system has the light source unit 19, a pair of optical fibers 55A and 55B connected to the light source unit 19, and wavelength conversion portions 57A and 57B disposed on light outgoing terminals of the optical fibers 55A and 55B respectively. The light source unit 19 has laser light sources LD1 and LD2 which are semiconductor light emitting devices, a light source control portion 59 for controlling and driving the laser light sources LD1 and LD2, a combiner 61 for combining outgoing lights from the laser light sources LD1 and LD2, a coupler 63 for branching the combined light into optical paths of two systems (the paired optical fibers 55A and 55B), an amplitude value setting portion 65 which will be described in detail later, and a driving signal generating portion 67. That is, the light source unit 19 functions as an illumination unit for supplying illumination light to a front end of the insertion portion of the endoscope.

The laser light sources LD1 and LD2 are connected in common to the light source control portion 59 so as to emit light in response to driving signals from one and the same light source control portion 59.

The optical fibers 55A and 55B guide laser lights emitted from the laser light sources LD1 and LD2, to the endoscope front end portion 39. The laser lights guided to the endoscope front end portion 39 generate white illumination light in which lights emitted from the wavelength conversion portions 57A and 57B are combined with the laser lights. The wavelength conversion portions 57A and 57B include fluorescent substances which are excited by the laser lights to thereby emit lights. The laser light sources LD1 and LD2 emit lights with desired intensities respectively in response to driving signals from the light source control portion 59 based on an instruction from an endoscope control portion 69 provided in the processor 21.

A memory 71 as a storage unit for storing imaging signals or various kinds of information and an image processing portion 73 are connected to the endoscope control portion 69. The endoscope control portion 69 controls the image processing portion 73 to perform suitable image processing on image data outputted from the imaging signal processing portion 53, and displays the processed image data on the display portion 15. In addition, the endoscope control portion 69 is connected to a not-shown network such as an LAN, for example, so as to distribute information including image data. Thus, the endoscope control portion 69 controls the endoscopic apparatus 100 as a whole.

The laser light source LD1 is a semiconductor laser which emits blue light with a center wavelength of 445 nm. The laser light source LD1 emits blue laser light which quantity of the emitted light is controlled by the light source control portion 59. The emitted light is irradiated to the wavelength conversion portions 57A and 57B of the endoscope front end portion 39 through the optical fibers 55A and 55B. For example, a broad-area type InGaN-based laser diode may be used as the laser light source LD1.

Figure 3:
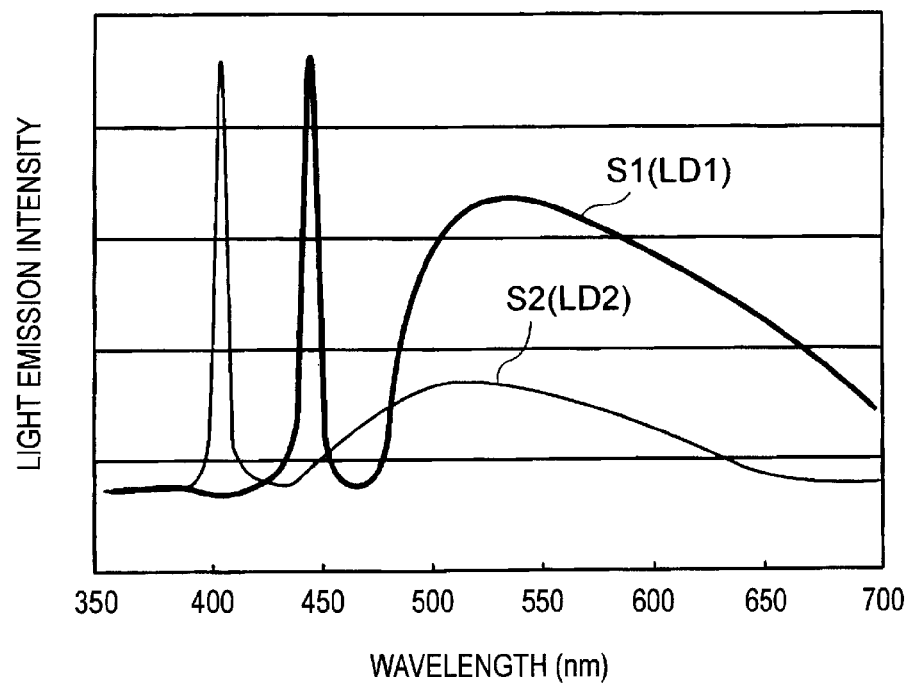
FIG. 3 is a graph showing spectral characteristics of outgoing light.

The wavelength conversion portions 57A and 57B include a plurality of kinds of fluorescent substances (such as YAGbased fluorescent substances or fluorescent substances containing BAM ($BaMgAl_{10}O_{37}$) etc.) which can absorb a part of the laser light emitted from the laser light source LD1 so as to be excited to emit green to yellow light. Thus, as shown in FIG. 3 which shows spectral characteristics of outgoing light, the laser light from the laser light source LD1 is combined with green to yellow excited light obtained by wavelength conversion of the laser light so as to generate white light shown by a profile S1.

The laser light source LD2 is a semiconductor laser which emits violet light with a center wavelength of 405 nm. The outgoing light quantity of laser light from the laser light source LD2 is also controlled in the same manner so as to be emitted from the light irradiation windows 43A and 43B of the endoscope front end portion 39. The light emitted from the laser light source LD2 is slightly wavelength-converted by the wavelength conversion portions 57A and 57B as compared with the light emitted from the laser light source LD1. Thus, the light from the laser light source LD2 is emitted as narrow-band light with a center wavelength of 405 nm as shown by a profile S2 in FIG. 3.

Next, the procedure of special light observation performed by the endoscopic apparatus 100 having the aforementioned configuration will be described.

The light source control portion 59 controls an outgoing light quantity of white illumination light from the laser light source LD1 (center wavelength 445 nm) and an outgoing light quantity of narrow-band light from the laser light source LD2 (center wavelength 405 nm) individually in response to an instruction from the endoscope control portion 69.

When the outgoing light quantity ratio between the laser light source LD1 and the laser light source LD2 is, for example, set as follows, different observation images can be obtained in the following cases respectively.

(1) When LD1:LD2 is set at 1:0, a white illumination image in a normal observation mode can be obtained.
(2) When LD1:LD2 is set at about 1:4, an observation image in which blood capillaries or microscopic patterns in a surface layer of a biological tissue are highlighted in a narrow-band observation mode can be obtained.
(3) When LD1:LD2 is set at about 7:1, an observation image in which capillary defects or microscopic patterns are displayed even in distant view in a narrow-band observation mode can be obtained.
(4) When LD1:LD2 is set at 0:1, a fluorescent observation image in a fluorescent observation mode can be obtained.

Figure 4:
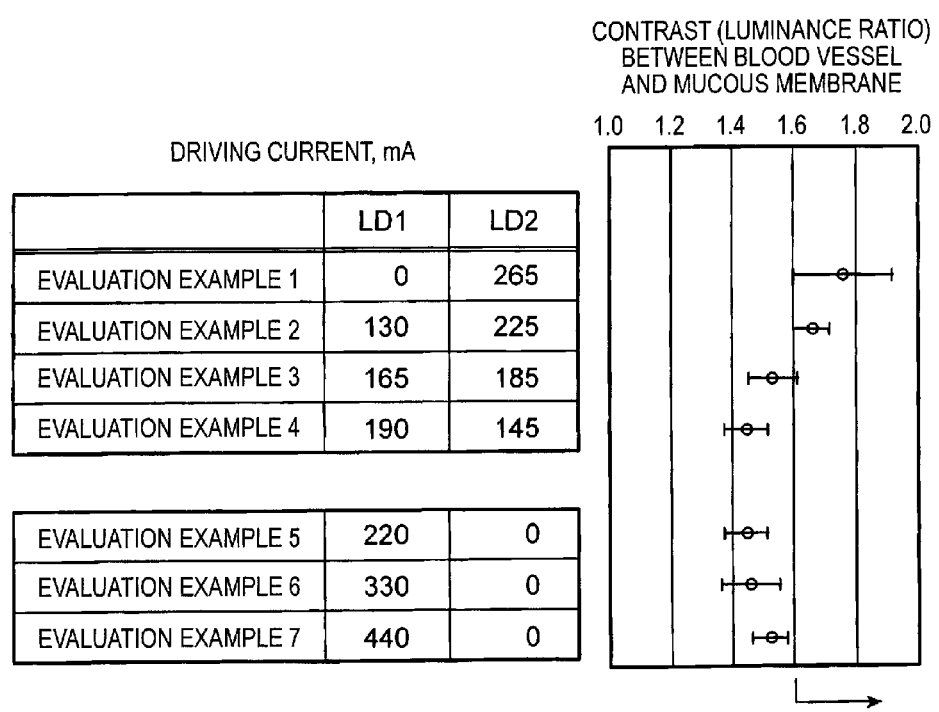
FIG. 4 is an explanatory view showing results of obtained contrasts (luminance ratios) between blood vessels and mucous membranes in accordance with outgoing light quantity ratios among laser light sources.

Here, FIG. 4 shows results of obtained contrasts (luminance ratios) between blood vessels and mucous membranes in accordance with outgoing light quantity ratios between the laser light sources LD1 and LD2 by way of example. As shown in Evaluation Example 1 to Evaluation Example 7, the contrast between a blood vessel (target to be observed) and a mucous membrane (background image) in each observation image ranges from 1.4 to 1.8 in accordance with change in outgoing light quantities of the laser light sources LD1 and LD2. Particularly in Evaluation Examples 1 and 2 where the contrast is not lower than 1.6, a satisfactory ability to extract surface-layer blood vessels can be obtained. Thus, there occurs a clear difference among observation images of a tissue surface layer in accordance with the outgoing light quantity ratio between the laser light sources LD1 and LD2.

In order to obtain a proper-exposure observation image in which information of a tissue surface layer is reflected well, it is therefore important to align the total outgoing light quantity of the outgoing light quantities of the laser light sources LD1 and LD2 to a target light quantity accurately while aligning the outgoing light quantity ratio between the laser light sources LD1 and LD2 to a desired light quantity ratio with high accuracy.

Figure 5:
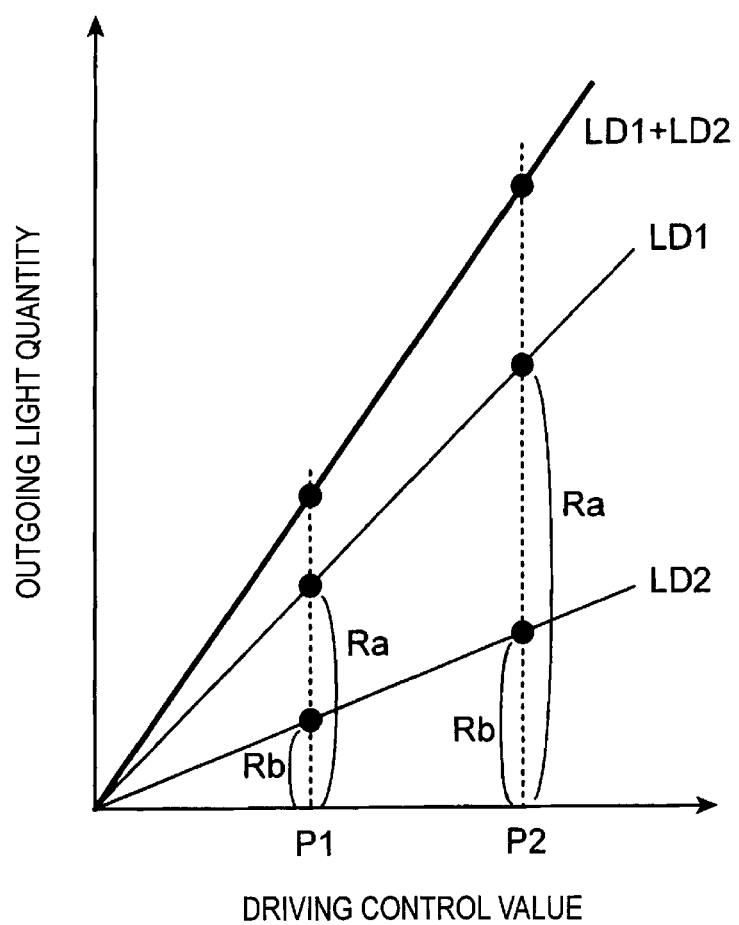
FIG. 5 is a graph showing the relation of outgoing light quantities of laser light sources to a target light quantity when the outgoing light quantity ratio is set at Ra:Rb.

As shown in FIG. 5 in which the relation of the outgoing light quantities of the laser light sources LD1 and LD2 to the target light quantity is shown when the outgoing light quantity ratio LD1:LD2 is set at Ra:Rb, the individual outgoing light quantities of the laser light sources LD1 and LD2 relative to their own target light quantities P1 and P2 are controlled so that the outgoing light quantity ratio Ra:Rb can be always kept constant even if the target light quantities P1 and P2 are changed. As a result, the total outgoing light quantity of the laser light sources LD1 and LD2 can be controlled in accordance with a desired target light quantity while the outgoing light quantity ratio between the laser light sources LD1 and LD2 is kept at a desired light quantity ratio.

Next, description will be made on the procedure to make control to increase/decrease the intensities of lights emitted from the laser light sources LD1 and LD2 in the endoscopic apparatus 100 in the aforementioned manner.

First, an operator pushes down an observation mode changeover button 30 which is provided in the body operation portion 23 of the endoscope 11 shown in FIG. 1 so as to function as a light quantity ratio setting unit and an observation mode selecting unit. Thus, the endoscope control portion 69 makes control to switch to one of various observation modes such as normal observation, narrow-band light observation or fluorescent observation. That is, in the normal observation mode, the outgoing light quantity ratio LD1:LD2 between the laser light sources LD1 and LD2 is set at 1:0. In the narrow-band light observation mode, the outgoing light quantity ratio LD1:LD2 is set at any preset ratio such as 1:4 or 7:1. In addition, in the fluorescent observation mode, the outgoing light quantity ratio LD1:LD2 is set at 0:1.

In the narrow-band light observation mode, control is made to keep both the outputs of the laser light sources LD1 and LD2 in the aforementioned outgoing light quantity ratio while setting the total outgoing light quantity of the laser light sources LD1 and LD2 at the target light quantity. The procedure to drive the laser light sources LD1 and LD2 to generate desired illumination light in the narrow-band light observation mode will be shown below.

First, the operator operates the observation mode changeover button 30 during observation with the endoscope. As a result, the endoscope control portion 69 sets an outgoing light quantity ratio in a desired observation mode. A plurality of kinds of outgoing light quantity ratios Ra:Rb between the laser light sources LD1 and LD2 are prepared and stored in the memory 71 in advance so as to be able to switch one outgoing light quantity ratio Ra:Rb to another by means of the observation mode changeover button 30. The endoscope control portion 69 reads an outgoing light quantity ratio Ra:Rb corresponding to the observation mode designated by the observation mode changeover button 30 and transmits the read outgoing light quantity ratio Ra:Rb to the light source control portion 59.

The light source control portion 59 receives information about the outgoing light quantity ratio Ra:Rb transmitted from the endoscope control portion 69, and uses the amplitude value setting portion 65 as an amplitude value setting unit to set amplitude values (current values) of individual driving signals for driving the laser light sources LD1 and LD2 based on the received outgoing light quantity ratio. Specifically, setting is made so that the current values of the individual driving signals of the laser light sources LD1 and LD2 are increased/decreased from standard driving current values respectively and integral intensity of the two individual driving signals is equal to integral intensity that can be obtained in the standard driving current values.

On the other hand, the target light quantity for the total light quantity obtained by summing up quantities of lights emitted from the laser light sources LD1 and LD2 is set by the endoscope control portion 69 based on a signal of a captured image from the imaging device 45.

The imaging signal processing portion 53 provided in the processor 21 shown in FIG. 1 receives RAW data outputted by the imaging device 45 of the endoscope 11 connected to the processor 21. The endoscope control portion 69 which also serves as a target light quantity setting unit outputs, to the light source control portion 59, information about target light quantity for controlling the driving signals of the laser light sources LD1 and LD2 so as to optimize an illumination light quantity in accordance with luminance information of the RAW data.

Figure 6:
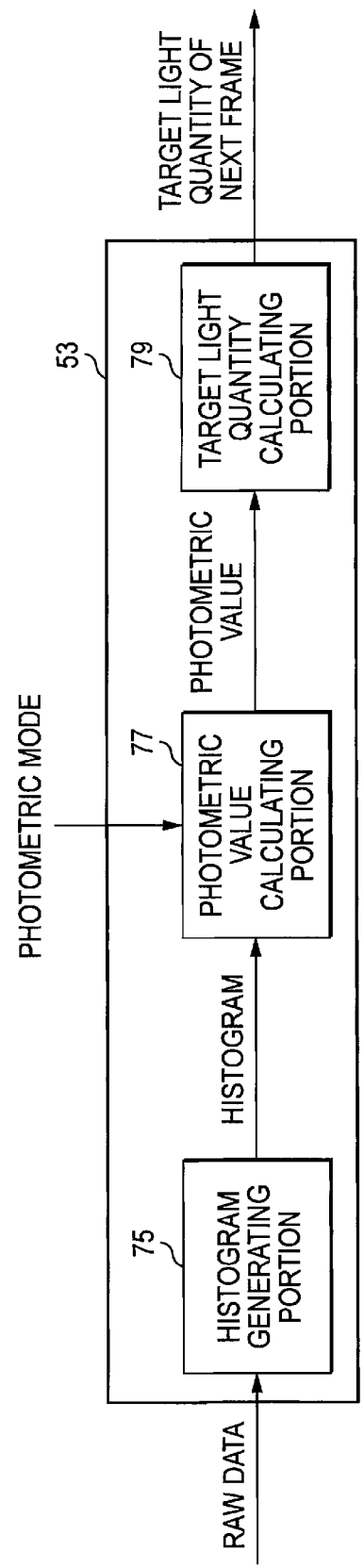
FIG. 6 is a block diagram of control by an imaging signal processing portion.

FIG. 6 shows a block diagram of control performed by the imaging signal processing portion 53. The RAW data (information of a raw image) outputted from the imaging device 45 is inputted to the imaging signal processing portion 53. A histogram generating portion 75 generates a histogram of light quantity corresponding to the RAW data and supplies the generated histogram to a photometric value calculating portion 77. The photometric value calculating portion 77 calculates a photometric value based on the supplied histogram and brightness detection values obtained by various photometric modes (peak value, mean value, etc.). A target light quantity calculating portion 79 obtains a target light quantity of the next frame in accordance with the calculated photometric value.

Values of target light quantities corresponding to luminance information of RAW data are stored in the memory 71 in advance. With reference to the memory 71, the endoscope control portion 69 obtains a target light quantity corresponding to the luminance information inputted from the imaging signal processing portion 53. The endoscope control portion 69 transmits the target light quantity to the light source control portion 59. The target light quantity is a value corresponding to an F-number of a background-art white light source such as a xenon lamp. The target light quantity is expressed, for example, in 12-bit gradation (0 to 4096).

Next, based on the amplitudes of the driving signals and the target light quantity set thus, individual driving signals of the laser light sources LD1 and LD2 are generated by common pulse modulation control. The light source control portion 59 transmits, to the driving signal generating portion 67, the amplitude values of the driving signals set by the amplitude value setting portion 65 and the information of the target light quantity for the total light quantity obtained by summing up the light quantities emitted from the laser light sources LD1 and LD2. The driving signal generating portion 67 obtains a signal of driving pulses pulse-modulated in accordance with the target light quantity, which will be described in detail later, and changes the amplitude of the driving pulses to the amplitude value set for each laser light source LD1, LD2 by the amplitude value setting portion 65.

That is, the signal of the driving pulses corresponding to the target light quantity is used in common, and amplitude values are changed respectively based on the common signal of the driving pulses to generate an individual driving signal for driving the laser light source LD1 and an individual driving signal for driving the laser light source LD2. The individual driving signal for driving the laser light source LD1 and the individual driving signal for driving the laser light source LD2 have wavelength patterns of driving pulses corresponding to the target light quantity but only their amplitude values thereof are different from each other. In this manner, driving pulses corresponding to the target light quantity are obtained in common for individual driving signals, and the amplitude values of the individual driving signals are set in accordance with the designated outgoing light quantity ratio. Thus, the total light quantity of lights emitted from the laser light sources LD1 and LD2 is matched with the target light quantity. When the target light quantity ratio is changed, the wavelength patterns of the driving pulses are changed in common while the amplitude value of each individual driving signal is fixed. Thus, the outgoing light quantity ratio can be kept constant in spite of pulse modulation control corresponding to the change of the target light quantity, so that the ratio between light quantities emitted from the laser light sources LD1 and LD2 can be prevented from being disturbed.

With the configuration in which driving pulses corresponding to a target light quantity are used in common among individual driving signals as described above, the modulation control of the individual control signals can be simplified as compared with the case where pulse modulation control is performed on individual control signals individually. In addition, even if a plurality of laser light sources are provided, pulse modulation control on each laser light source corresponding to the target light quantity ratio can be shared among all the laser light sources so as to prevent a driving circuit from being complicated.

Next, description will be made in a specific example in which driving pulses corresponding to the target light quantity for a total light quantity of lights emitted from the laser light sources LD1 and LD2 are obtained by pulse modulation control used in common between the laser light sources LD1 and LD2.

The light source control portion 59 shown in FIG. 1 performs pulse lighting control on the outgoing light quantities of the laser light sources LD1 and LD2 with predetermined driving pulses in response to an instruction from the endoscope control portion 69. The driving pulses are generated by the endoscope control portion 69 referring to the memory 71. The driving pulses are controlled by use of three kinds of controls including PNM (Pulse Number Modulation), PDM (Pulse Density Modulation) and PWM (Pulse Width Modulation)

Figure 7:
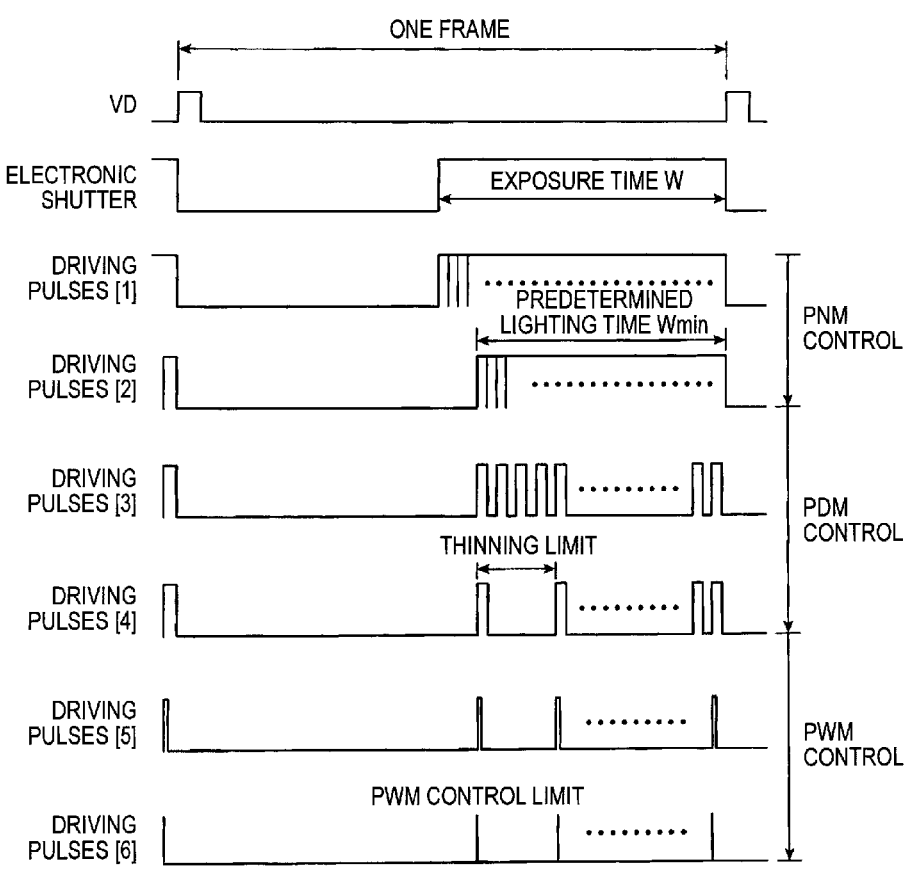
FIG. 7 is a timing chart in an example of control of driving pulses.

FIG. 7 shows a timing chart of an example for controlling driving pulses. The maximum light quantity is obtained by driving pulses [1] which enable lighting all over an exposure time W of an electronic shutter in a period of one frame of an image defined by a vertical sync signal VD. Here, assume that the period of one frame is 33 ms, and the shutter speed is 1/60 s. In addition, assume that the frequency of the driving pulses [1] is 120 kHz, and 2,000 pulses are included in the exposure time of the electronic shutter.

Assume that the light quantity is decreased from the maximum light quantity provided by the driving pulses [1]. In this case, the PNM control, the PDM control and the PWM control are performed in first to third pulse modulation regions respectively in descending order of light quantity, so that the light quantity is decreased gradually.

First, in the PNM control, the number of pulses is reduced in a rear-aligned manner in the temporal axis all over the exposure time W of the electronic shutter so that the lighting time is shortened. That is, the number of driving pulses is reduced to delay the drive start timing till the number of driving pulses reaches a predetermined minimum ratio to the exposure time of the electronic shutter in one frame, as shown in driving pulses [2]. Thus, the lighting time of the laser light source is shortened. Incidentally, the maximum light quantity does not have to correspond to lighting all over the exposure time W of the electronic shutter but may correspond to lighting all over the time for one frame or may correspond to continuous lighting.

Next, as shown in driving pulses [3], the lighting time of the laser light source is shortened to a predetermined lighting time Wmin by the PNM control, and the driving pulses are then thinned by the PDM control. In the PDM control, the driving pulses are thinned at predetermined intervals in the lighting time shortened to the predetermined lighting time Wmin, so that the pulse density within the lighting time is reduced.

As shown in driving pulses [4], the PDM control is performed till the pulse interval of the driving pulses reaches a thinning limit, that is, till the driving pulses have a predetermined minimum pulse density.

Next, as shown in driving pulses [5], the pulse width of each driving pulse is reduced by the PWM control after the driving pulses reach a predetermined minimum number of pulses. Then, as shown in driving pulses [6], the PWM control is performed till the pulse width of each driving pulse reaches a PWM control limit, that is, till the pulse width reaches a predetermined minimum pulse width.

Figure 8:
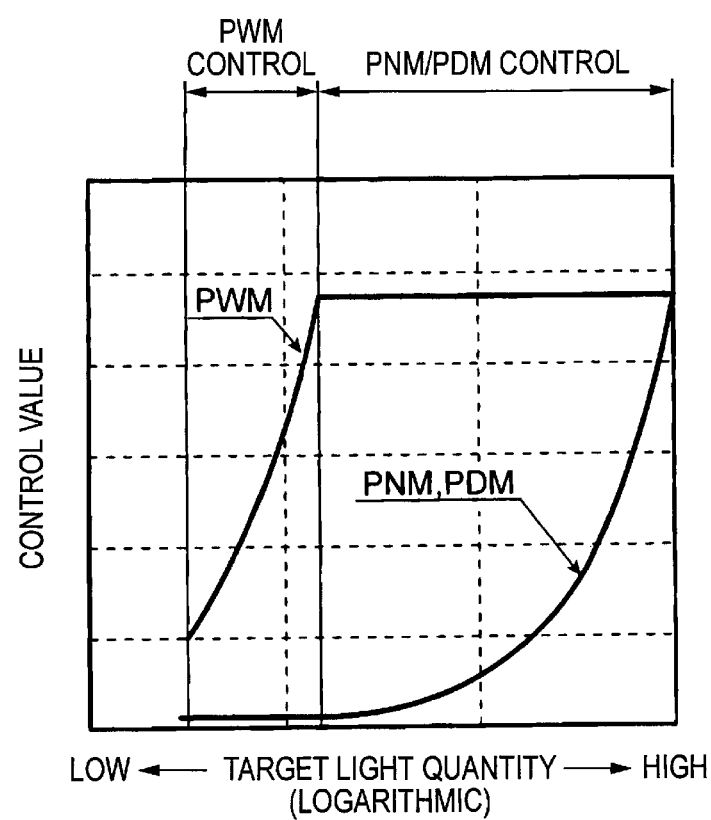
FIG. 8 is a graph showing contents of pulse control on each light quantity from a maximum light quantity to a minimum light quantity.

The aforementioned contents of information of control parameters for light quantity ranging from the maximum light quantity to the minimum light quantity are shown in a lump in FIG. 8 and Table 1. The information of control parameters shown in FIG. 8 and Table 1 is stored in the memory 71 shown in FIG. 1, and referred to at any time by the endoscope control portion 69 so that desired driving pulses are generated.

TABLE 1

| Light Quantity | PNM/PDM (Number of Pulses) | PWM (%) |
| --- | --- | --- |
| Maximum | 2000 | 95 |
| ↑ | (PNM) | 95 |
| | 144 | 95 |
| | (PDM) | 95 |
| | 16 | 95 |
| | 16 | ↓ |
| Minimum | 16 | 7.8 |

Thus, in performing control to reduce the light quantity, the PNM control is first performed on the maximum light quantity so that it is possible to shorten the lighting time of the laser light source to thereby suppress occurrence of blurring of a captured image caused by shaking. In addition, the non-lighting time of the laser light source is expanded to obtain an effect to reduce heat generated by the light source itself or each optical member on the optical path as compared with the case of continuous lighting.

In addition, control is switched from the PNM control to the PDM control as soon as the lighting time is shortened to the predetermined lighting time. It is therefore possible to keep a moderate lighting time (144 pulses in the aforementioned example) to thereby suppress flicker during observation of a motion picture.

The number of pulses (16 pulses in the aforementioned example) which is a lower limit in the PDM control can prevent the dimming resolution from being roughed by the PDM control.

The PDM control is performed till the thinning limit of the driving pulses, and control is switched from the PDM control to the PWM control to further reduce the target light quantity. In this PWM control, the duty ratio of each driving pulse is changed so that the light quantity can be adjusted more finely in a range of the light quantity which is lower than the thinning limit. Thus, the dimming resolution is improved.

In the pulse lighting control over the laser light source, speckle noise may cause unevenness in illumination with the laser light source. The speckle noise can be reduced by high frequency modulation driving. In this example of control, driving is always performed with pulses of 120 kHz. An upper limit of the duty ratio in the PWM control is set at 95% in order to obtain a satisfactory effect to reduce the speckle noise.

And, real laser light cannot faithfully follow a rising signal for driving, but rises with a certain delay component. In the same manner, the laser light also has a delay component at trailing time. It is therefore expected that each driving pulse will trail before reaching a target value if the driving pulse is extremely narrow in width. Accordingly, the lower limit value of the duty ratio is set at 7.8% in order to perform the PWM control correctly.

The PNM/PDM control and the PWM control are changed over in accordance with a target light quantity, and each control is used exclusively from any other control. A controllable dynamic range of light quantity is 13.9:1 in the PNM control ranging from a maximum value 2,000 to a minimum value 144, 9:1 in the PDM control ranging from a maximum value 144 to a minimum value 16, 12.2:1 in the PWM control ranging a maximum value 95% to a minimum value 7.8%, and 5:1 in the current value control ranging from a maximum value 1 to a minimum value 0.2. Accordingly, the controllable dynamic range reaches 1526:1 in the combination of these controls.

When an equivalent dynamic range and an equivalent dimming resolution to those described above are obtained only by PNM control, the pulse frequency is about 14.6 MHz (60 Hz×1526×16), and a high-speed drive circuit for the laser light source is required. In the same manner, when the dynamic range and the dimming resolution are obtained only by the PWM control, the pulse width control resolution is about 0.34 ns (1/(120 k×1526×16)), and a control circuit operating at 3 GHz is required. Thus, the drive unit for the laser light source can be simplified on a large scale by control with PNM control and PDM control selected in accordance with each dimming range, as compared with a method for controlling light quantity by PNM control alone or PWM control alone.

It is preferable that the endoscope control portion 69 (see FIG. 1) detects brightness based on RAW data from the imaging device 45 and various photometric modes, and the quantity of light emitted from each laser light source is set in consideration of the following points to calculate a target light quantity in a next frame.

(1) Total Light Quantity Limit

Temperature of each laser light source is detected. When the detected temperature is beyond a specified temperature, correction control is performed to subtract a predetermined value from an intended light quantity control value. On the contrary, when the detected temperature is in a normal temperature range, a predetermined value is added to the light quantity control value which has been controlled to decrease, so that the light quantity control value is brought back to the intended light quantity control value before correction. This correction control is performed to limit heat generated in the endoscope front end portion.

(2) Individual Difference Correction of Optical Components

In order to correct difference among models of optical components, the light quantity control value of each laser light source after control of the total light quantity of the apparatus is multiplied by a coefficient corresponding to the laser light source. The coefficients of the laser light sources are set to make the total sum of the coefficients constant to thereby keep the total light quantity constant. Since the combiner 61 (see FIG. 1) is used in this configuration, this correction may be dispensed with. When irradiation with light is performed from a plurality of laser light sources individually, the light quantity control values of the laser light sources have to be corrected.

According to the illumination unit and the endoscopic apparatus provided with the same, as described above, the outgoing light quantity from each of a plurality of laser light sources can be controlled with high accuracy in accordance with a target light quantity without breaking the balance in outgoing light quantity ratio among the laser light sources. In addition, use of semiconductor light sources leads to high responsiveness and stability. As a result, illumination light of an endoscope in normal observation or special light observation can be set accurately at any intensity so that a desired observation image can be always obtained.

In addition, the endoscopic apparatus configured thus can control the light sources equivalently to an existing configuration using a xenon lamp or the like. It is therefore possible to use an existing processor as it is, so that it is possible to enhance the general purpose of the configuration. The semiconductor light sources have much longer lives as light sources than the xenon lamp or the like. It is therefore possible to lighten the maintenance of the apparatus.

In addition, a laser light source or a light emitting diode with a center wavelength of 360 to 530 nm can be used as the semiconductor light source for illumination of narrow-band light, so that an image where blood capillaries or microscopic structures in a biological tissue surface layer are highlighted can be obtained. In any mode, high-luminance illumination light can be obtained with saved power.

In this manner, the invention is not limited to the aforementioned embodiment, but the invention is intended to cover modifications and applications which can be performed by those skilled in the art based on the description of this specification and well-known techniques. Thus, such modifications and applications are included in the scope of the invention claimed for protection. For example, although description has been made in the case where a laser light source is used as a semiconductor light source by way of example, a configuration using a light emitting diode may be arranged. In addition, light quantity may be controlled by combination of exposure control using an electronic shutter of an imaging unit and light quantity control of a light source. Although description has been made above on the control of outgoing light quantities of two semiconductor light sources, the number of light sources is not limited to two, but any number of light sources may be arranged. Further, the outgoing light quantities may be controlled by amplitudes of driving voltage values in place of amplitudes of driving current values.

The following items are disclosed in this specification as described above.

(1) An illumination unit includes a plurality of semiconductor light sources, a target light quantity setting unit, a light quantity ratio setting unit, an amplitude value setting unit and a driving signal generating unit. The plurality of semiconductor light sources emit lights with different spectra from each other in accordance with inputted driving signals. The target light quantity setting unit sets a target light quantity for a total outgoing light quantity which is obtained by summing up quantities of the lights emitted from the semiconductor light sources. The light quantity ratio setting unit sets an outgoing light quantity ratio among the semiconductor light sources. The amplitude value setting unit sets amplitude values of driving signals for the semiconductor light sources, respectively, based on the set outgoing light quantity ratio. The driving signal generating unit generates the driving signals by use of common pulse modulation control corresponding to the target light quantity while keeping the set amplitude values.

According to the illumination unit, amplitude values of driving signals are set in accordance with the outgoing light quantity ratio, and the driving signals are generated by common pulse modulation control corresponding to a target light quantity while keeping the set amplitude values. Thus, the pulse modulation control corresponding to the target light quantity can be performed with the fixed outgoing light quantity ratio. Thus, the balance in outgoing light quantity ratio among the semiconductor light sources can be prevented from being broken.

(2) In the illumination unit according to (1), the semiconductor light sources are connected to one and the same driving signal generating unit so as to share the driving signal generating unit.

According to the illumination unit, the semiconductor light sources are connected to one and the same driving signal generating unit so that the semiconductor light sources can emit light in response to driving signals from one and the same driving signal generating unit. Due to this configuration, a driving circuit can be simplified.

(3) In the illumination unit according to (1) or (2), the amplitude values of the driving signals are set by increase/decrease of driving current values.

According to the illumination unit, a driving current value is increased/decreased to adjust the amplitude of each driving signal. In this manner, the outgoing light quantity ratio can be set with high accuracy by simple current control.

(4) In the illumination unit according to any one of (1) through (3), the semiconductor light sources include a white light source for generating white light and a narrow-band light source for generating narrow-band light in a predetermined wavelength band.

According to the illumination unit, the outgoing light quantity ratio between the white light source for normal observation and the narrow-band light source for special light observation is changed to combine an image obtained by the normal observation with an image obtained by the special light observation at a desired ratio. Thus, a desired endoscopically diagnostic image can be obtained.

(5) In the illumination unit according to (4), the narrow-band light source emits narrow-band light with a center wavelength of 360 to 530 nm.

According to the endoscopic apparatus, narrow-band light in a visible short wavelength band with a center wavelength of 360 to 530 nm is used so that it is possible to obtain an image in which blood capillaries or microscopic structures in a biological tissue surface layer are highlighted.

(6) In the illumination unit according to (4) or (5), the white light source includes a laser light source and fluorescent substances which emit light in response to light emitted from the laser light source. The light emitted from the laser light source and the light emitted from the fluorescent substances are mixed to generate white illumination light.

According to the endoscopic apparatus, illumination light with a desired spectrum such as white light can be obtained stably with high light quantity controllability by the laser light sources which have long lives as light sources.

(7) An endoscopic apparatus includes an illumination optical system and an imaging optical system. The illumination optical system outgoes light emitted from the illumination unit according to any one of (1) through (6), from a front end of an endoscope insertion portion. The imaging optical system obtains an observation image of a subject.

According to the endoscopic apparatus, illumination light emitted toward a subject can be supplied without breaking balance in outgoing light quantity ratio among the semiconductor light sources so that an observation image in which a feature quantity is highlighted can be obtained as intended.

(8) The endoscopic apparatus according to (7) further includes an imaging unit. The imaging unit captures an image of the subject with an exposure time adjusted by an electronic shutter. The driving signal generating unit performs pulse modulation control including a first pulse modulation control period, a second pulse modulation control period and a third pulse modulation control period in descending order of the target light quantity. In the first pulse modulation control period, the number of the driving pulses is reduced until a predetermined lighting time to shorten a lighting time of the semiconductor light sources for the exposure time of the electronic shutter within one frame. In the second pulse modulation control period, the driving pulses are thinned at predetermined intervals for a predetermined lighting time in the first pulse modulation control period to reduce pulse density in the predetermined lighting time. In the third pulse modulation control period, a pulse width of each of the driving pulses whose pulse number is minimized in the second pulse modulation control period is reduced.

According to the endoscopic apparatus, the driving signal generating unit performs pulse modulation including the first to third pulse modulation control periods in descending order of target light quantity. As a result, when the target light quantity is high, the control for shortening the lighting time of the light sources can be made by priority, so that image blurring in a captured image can be suppressed and heat generation can be reduced. On the contrary, when the target light quantity is low, a plurality of pulses are present in a predetermined lighting time. Thus, occurrence of flicker can be suppressed.

(9) The endoscopic apparatus according to (7) or (8), further includes an observation mode selecting unit. The observation mode selecting unit selects one observation mode from a plurality of observation modes having different targets to be highlighted in the observation image. The light quantity ratio setting unit sets the outgoing light quantity ratio in accordance with the selected observation mode.

According to the endoscopic apparatus, a specific outgoing light quantity ratio is selected in accordance with an observation mode so that the outgoing light quantities of the semiconductor light sources can be controlled in the selected outgoing light quantity ratio. Thus, by a simple method of selecting an observation mode, the outgoing light quantities of the semiconductor light sources can be controlled in an outgoing light quantity ratio optimized for the selected observation mode.

(10) The endoscopic apparatus according to any one of (7) to (9) further includes a light quantity detecting unit. The light quantity detecting unit detects a light quantity of an image of the subject based on an imaging signal outputted from the imaging unit. The target light quantity setting unit sets the target light quantity based on the light quantity detected by the light quantity detecting unit.

According to the endoscopic apparatus, the target light quantity is set based on the luminance information of a captured observation image, so that the light quantity in the next imaging time can be made proper.

What is claimed is:

1. An illumination unit comprising:
a plurality of semiconductor light sources that emit lights with different spectra from each other in accordance with inputted driving signals;
a target light quantity setting unit that sets a target light quantity for a total outgoing light quantity which is obtained by summing up quantities of the lights emitted from the semiconductor light sources;
a light quantity ratio setting unit that sets an outgoing light quantity ratio among the semiconductor light sources;
an amplitude value setting unit that sets amplitude values of individual driving signals for the semiconductor light sources to different values, respectively, based on the set outgoing light quantity ratio; and
a driving signal generating unit that obtains a common signal of a common driving pulse corresponding to the target light quantity, modulates the common signal in common pulse modulation control, and changes an amplitude value of the modulated common signal to the amplitude values set by the amplitude value setting unit for the semiconductor light sources to generate individual driving signals for the respective semiconductor light sources while keeping the set amplitude values,
wherein the common pulse modulation control is selected from at least one of the pulse number modulation, pulse density modulation, and pulse width modulation.

2. The illumination unit according to claim 1, wherein:
the semiconductor light sources are connected to one and the same driving signal generating unit so as to share the driving signal generating unit.

3. The illumination unit according to claim 1, wherein:
the amplitude values of the driving signals are set by increase/decrease of driving current values.

4. The illumination unit according to claim 1, wherein:
the semiconductor light sources include a white light source for generating white light and a narrow-band light source for generating narrow-band light in a predetermined wavelength band.

5. The illumination unit according to claim 4, wherein:
the narrow-band light source emits narrow-band light with a center wavelength of 360 to 530 nm.

6. The illumination unit according to claim 4, wherein:
the white light source includes a laser light source and fluorescent substances which emit light in response to light emitted from the laser light source; and
the light emitted from the laser light source and the light emitted from the fluorescent substances are mixed to generate white illumination light.

7. An endoscopic apparatus comprising:
an illumination optical system by which light emitted from the illumination unit according to claim 1 is made to outgo from a front end of an endoscope insertion portion; and
an imaging optical system that obtains an observation image of a subject.

8. The endoscopic apparatus according to claim 7, further comprising:
an imaging unit that captures an image of the subject; and
an electronic shutter that adjusts an exposure time of the imaging unit; wherein:
the driving signal generating unit performs pulse modulation control including a first pulse modulation control period, a second pulse modulation control period and a third pulse modulation control period in descending order of the target light quantity;

in the first pulse modulation control period, the number of the driving pulses is reduced until a predetermined lighting time to shorten a lighting time of the semiconductor light sources for the exposure time of the electronic shutter within one frame;

in the second pulse modulation control period, the driving pulses are thinned at predetermined intervals for a predetermined lighting time in the first pulse modulation control period to reduce pulse density in the predetermined lighting time; and in the third pulse modulation control period, a pulse width of each of the driving pulses whose pulse number is minimized in the second pulse modulation control period is reduced.

9. The endoscopic apparatus according to claim 7, further comprising:

an observation mode selecting unit that selects one observation mode from a plurality of observation modes having different targets to be highlighted in the observation image; wherein:

the light quantity ratio setting unit sets the outgoing light quantity ratio in accordance with the selected observation mode.

10. The endoscopic apparatus according to claim 7, further comprising:

a light quantity detecting unit that detects a light quantity of an image of the subject based on an imaging signal outputted from the imaging unit; wherein:

the target light quantity setting unit sets the target light quantity based on the light quantity detected by the light quantity detecting unit.

\* \* \* \* \*